US009895955B2

(12) United States Patent
Quaranta-Guido

(10) Patent No.: US 9,895,955 B2
(45) Date of Patent: Feb. 20, 2018

(54) METHOD FOR CONTROLLING INTERIOR VEHICLE TEMPERATURE TO PROTECT OCCUPANTS FROM EXTREME HEAT

(71) Applicant: Sandra Quaranta-Guido, Lake Hopatcong, NJ (US)

(72) Inventor: Sandra Quaranta-Guido, Lake Hopatcong, NJ (US)

(*) Notice: Subject to any disclaimer, the term of this patent is extended or adjusted under 35 U.S.C. 154(b) by 0 days.

(21) Appl. No.: 15/342,572

(22) Filed: Nov. 3, 2016

(65) Prior Publication Data

US 2017/0050490 A1 Feb. 23, 2017

Related U.S. Application Data

(63) Continuation-in-part of application No. 14/487,620, filed on Sep. 16, 2014, now Pat. No. 9,513,173.

(51) Int. Cl.

| *B60H 1/00* | (2006.01) |
| *B60Q 9/00* | (2006.01) |
| *G01S 19/13* | (2010.01) |
| *G01N 33/00* | (2006.01) |
| *G01K 1/02* | (2006.01) |
| *G01K 3/00* | (2006.01) |

(52) U.S. Cl.
CPC ......... *B60H 1/00778* (2013.01); *B60H 1/008* (2013.01); *B60H 1/00792* (2013.01); *B60H 1/00821* (2013.01); *B60H 1/00985* (2013.01); *B60Q 9/00* (2013.01); *G01K 1/024* (2013.01); *G01K 1/026* (2013.01); *G01K 3/005* (2013.01); *G01N 33/004* (2013.01); *G01S 19/13* (2013.01); *G01K 2205/00* (2013.01)

(58) Field of Classification Search
CPC .................................................. B60H 1/00735
See application file for complete search history.

(56) References Cited

U.S. PATENT DOCUMENTS

| 6,496,106 | B1 | 12/2002 | Rodriguez |
| 7,081,811 | B2 | 7/2006 | Johnson et al. |
| 9,227,484 | B1 * | 1/2016 | Justice ................. B60N 2/002 |
| 2003/0098784 | A1 | 5/2003 | Van Bosch et al. |
| 2005/0038582 | A1 * | 2/2005 | Arndt ................... B60H 1/008 |
| | | | 701/31.4 |
| 2005/0061563 | A1 | 3/2005 | Syed |
| 2006/0179853 | A1 * | 8/2006 | Vosburgh .......... B60H 1/00742 |
| | | | 62/126 |
| 2010/0181959 | A1 * | 7/2010 | Gibbs ................ F02N 11/0866 |
| | | | 320/104 |

\* cited by examiner

*Primary Examiner* — Imran K Mustafa
(74) *Attorney, Agent, or Firm* — Maier & Maier, PLLC

(57) ABSTRACT

A method for protecting occupants in the passenger compartment of a parked motor vehicle from exposure to dangerously elevated temperatures and $CO_2$ concentration levels is based on control of vehicle systems by a central microprocessor in communication with $CO_2$ and temperature sensors and a wireless communication module. The method implements a graduated, progressive series of warnings and responses as the cabin temperature and/or $CO_2$ concentration levels reach certain designated setpoints, so that security-compromising steps, such as opening windows, can be deferred until less extreme measures have been exhausted.

10 Claims, 3 Drawing Sheets

METHOD FOR CONTROLLING INTERIOR VEHICLE TEMPERATURE TO PROTECT OCCUPANTS FROM EXTREME HEAT

CROSS-REFERENCE TO RELATED APPLICATIONS

This application is a continuation-in-part of U.S. patent application Ser. No. 14/487,620, filed Sep. 16, 2014, and entitled Method for Controlling Interior Vehicle Temperature to Protect Occupants from Extreme Heat, the entire contents of which are hereby incorporated by reference in their entirety.

FIELD OF INVENTION

The present invention relates to the field of systems for monitoring and controlling the climate in a passenger compartment of a motor vehicle, and more particularly to systems for preventing hazardous conditions in an occupied passenger compartment of a parked motor vehicle.

BACKGROUND

Due to the greenhouse effect, life-threatening temperatures can develop very rapidly inside the passenger cabin of a parked motor vehicle when ambient temperatures exceed 75° F. Animals and small children confined in a car with the windows closed will succumb to heat exhaustion in a matter of minutes as the cabin temperature exceeds 110° F. Deaths of children and pets from heat exposure in parked vehicles are recurring tragedies that can be avoided with suitable prevention systems. The development of advanced central microprocessor systems capable of monitoring and controlling all vehicle systems in newer vehicles provides a means by which cabin temperatures can be monitored and maintained within a safe range.

The need to respond rapidly to cabin over-heating in an occupied parked vehicle must be balanced, however, with the need to preserve the security of the occupants, who are often infants and pets. For example, immediately opening windows and unlocking doors when a temperature increase is detected may leave an infant exposed to abduction or enable a pet to escape. Therefore, there is a need for a system which implements a graduated, progressive series of warnings and responses as the cabin temperature reaches certain designated setpoints, so that security-compromising steps can be deferred until less extreme measures have been exhausted.

SUMMARY OF THE INVENTION

The present invention is a method for protecting occupants in a passenger compartment of a parked motor vehicle from exposure to dangerously elevated temperatures and concentration levels of carbon dioxide ($CO_2$). To implement this method, the vehicle must be equipped with a central microprocessor, or equivalent central CPU or computer system, which is capable of monitoring the status of and controlling the operations of the major vehicle systems, including engine, power train, electrical (including batteries), climate controls (including fans), windows, doors, horns, alarms, lights, and navigation (including GPS).

The vehicle must also be equipped with multiple $CO_2$ sensors and temperature sensors. These sensors should be distributed within the passenger compartment so as to monitor cabin conditions and generate representative data on $CO_2$ concentration and temperature. These sensors have interfaces with the central microprocessor, which controls sensor operations and receives the $CO_2$ and temperature data generated by the sensors.

The vehicle is also equipped with a wireless communication module, also having an interface with the central microprocessor, which controls its operations so that wireless warning messages can be sent to designated contacts.

A $CO_2$ concentration indicative of the presence of one or more occupants in the passenger compartment is determined and is stored in the central microprocessor. Also established and stored in the central microprocessor are a progressive series of emergency response temperature setpoints, comprising a lowest first temperature setpoint, a maximum temperature setpoint, and one or more intermediate temperature setpoints between the first temperature setpoint and the maximum temperature setpoint.

For example, there can be three programmed emergency response temperature setpoints, based on a maximum temperature setpoint of 110° F., with the first temperature setpoint at 80% of the maximum, or 88° F., and the second temperature setpoint at 90% of the maximum, or 99° F.

A progressive series of emergency warning messages and emergency response actions are formulated and stored in the central microprocessor. For each emergency response temperature setpoint there are one or more corresponding warning messages and one or more corresponding response actions. Hence, in the example cited above, there would be a set of initial warning messages and initial response actions to be implemented when the cabin temperature reaches the first setpoint of 88° F., and a set of interim warning messages and interim response actions to be implemented when the cabin temperature reaches the second setpoint of 99° F., and a set of final warning messages and final response actions to be implemented when the cabin temperature reaches the maximum setpoint of 110° F.

The $CO_2$ sensors are activated when the central microprocessor determines, based on its monitoring of the status of vehicle systems, such as the engine, the drive train and the climate control system, that the vehicle is parked and the climate control system is not operating. The central microprocessor then compares the generated $CO_2$ concentration data with the established activation $CO_2$ concentration level, and when that level is equaled or exceeded, it activates the temperature sensors, which generate temperature data for the passenger compartment.

The central microprocessor next compares the generated temperature data with the emergency response temperature setpoints. When each temperature setpoint is equaled or exceeded, the corresponding warning messages are sent to corresponding designated contacts through the wireless communications module, and the central microprocessor implements the initial response actions through one or more of the vehicle systems.

Referring to our previous example, when the cabin temperature reaches the first setpoint of 88° F., the vehicle owner and his/her family members could be notified by text messages, and one or more fans could be activated to circulate ambient air through the passenger compartment.

Then, when the cabin temperature reaches the second setpoint of 99° F., a second warning message could be sent to the owner and his/her family, and the central emergency microprocessor could also send a 911 emergency text or call, including GPS coordinates for the vehicle location. The central microprocessor could also activate some or all of the vehicle's climate control features, such as air-conditioning, initially on battery power, but switching to engine power when the battery has discharged below a designated level. Finally, when the cabin temperature reaches the allowed maximum of 110° F., a third series of warning messages, including emergency/911 messages with GPS coordinates, could be sent, and the central microprocessor could implement final response actions, such as opening windows, unlocking doors, sounding alarms, and flashing emergency lights.

Alternatively, the central microprocessor may trigger emergency response actions without the activation of the temperature sensors by monitoring increasing levels of $CO_2$ concentration within the passenger compartment. The $CO_2$ sensors may be activated once the central microprocessor determines, based on its monitoring of the status of the vehicle systems, such as the engine, the drive train and the climate control system, that the vehicle is parked and the climate control system is not operating. The central microprocessor can then compare $CO_2$ concentration data with the established activation $CO_2$ level to determine the presence of any occupants in the passenger compartment. The presence of at least one occupant is detected when the generated $CO_2$ concentration measurement equals or exceeds the established activation $CO_2$ concentration level.

When the presence of at least one occupant is detected, the central microprocessor may then continuously monitor the $CO_2$ concentration levels within the passenger compartment and compare them to emergency response $CO_2$ concentration setpoints stored therein. The emergency response $CO_2$ concentration setpoints may include a first $CO_2$ concentration setpoint, a maximum $CO_2$ concentration setpoint, and one or more intermediate $CO_2$ concentration setpoints ranging between the first and maximum $CO_2$ concentration setpoints. When the central microprocessor determines that the $CO_2$ concentration level within the passenger compartment equals or exceeds a first $CO_2$ concentration setpoint, the central microprocessor initiates the first of a progressive series of emergency response actions stored within the central microprocessor.

Different emergency response actions may correspond to each of the emergency response $CO_2$ concentration setpoints. The emergency response actions may include sending wireless messages to designated contacts through the wireless communications module, controlling a mechanical response through one or more of the vehicle systems, or implementing any other safety precaution as is known by a person having ordinary skill in the art. When each of the $CO_2$ concentration setpoints is equaled or exceeded, the corresponding emergency response actions are initiated by the central microprocessor.

Another exemplary embodiment described herein provides the simultaneous monitoring of both the $CO_2$ concentration levels and temperature data within the passenger compartment of the vehicle. When at least one occupant is detected while the vehicle is parked and the climate control system is not operating, the central microprocessor may monitor both the temperature sensors and $CO_2$ sensors. If either the temperature data generated by the temperatures sensors or the $CO_2$ concentration levels generated by the $CO_2$ sensors equal or exceed the preprogrammed emergency setpoints corresponding to each, the central microprocessor may initiate emergency response action(s).

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION OF THE PREFERRED EMBODIMENT

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
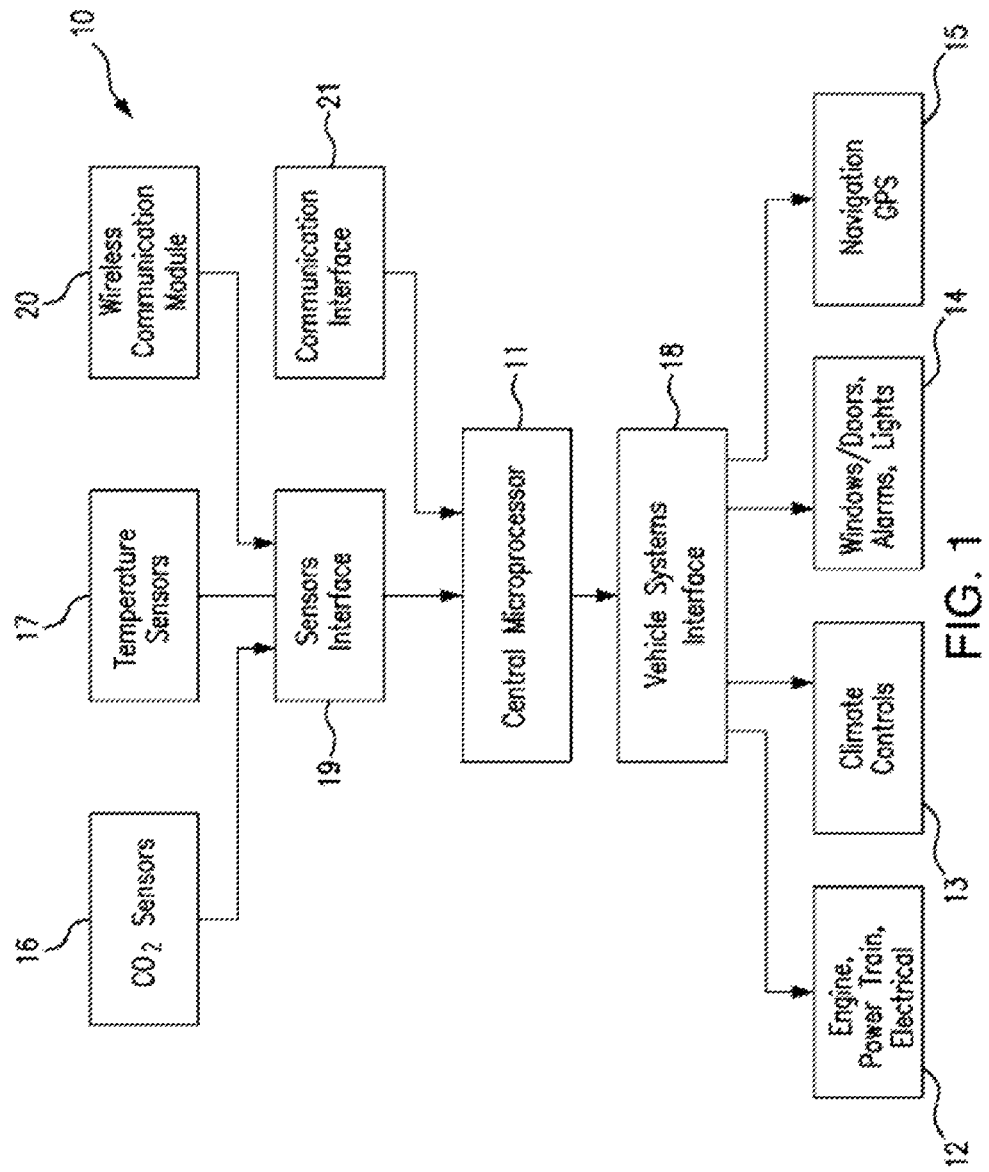
FIG. 1 is a schematic diagram of the control, sensor, interface and communication features of one embodiment of the present invention.

FIG. 1 schematically depicts the vehicle equipment required to implement one embodiment of the passenger compartment temperature protection method of the present invention 10. A central microprocessor 11 monitors and controls multiple vehicle systems, including engine, power train and electrical systems 12, climate control systems 13, window, door, alarm and light systems 14, and navigation/GPS systems 15, through a vehicle systems interface 18.

The central microprocessor also controls and monitors multiple $CO_2$ sensors 16 and temperature sensors 17, through a sensors interface 19. Wireless messages, as text or voice, are sent by the central microprocessor 11 through a communication interface 12 to a wire communication module 21.

Figure 2:
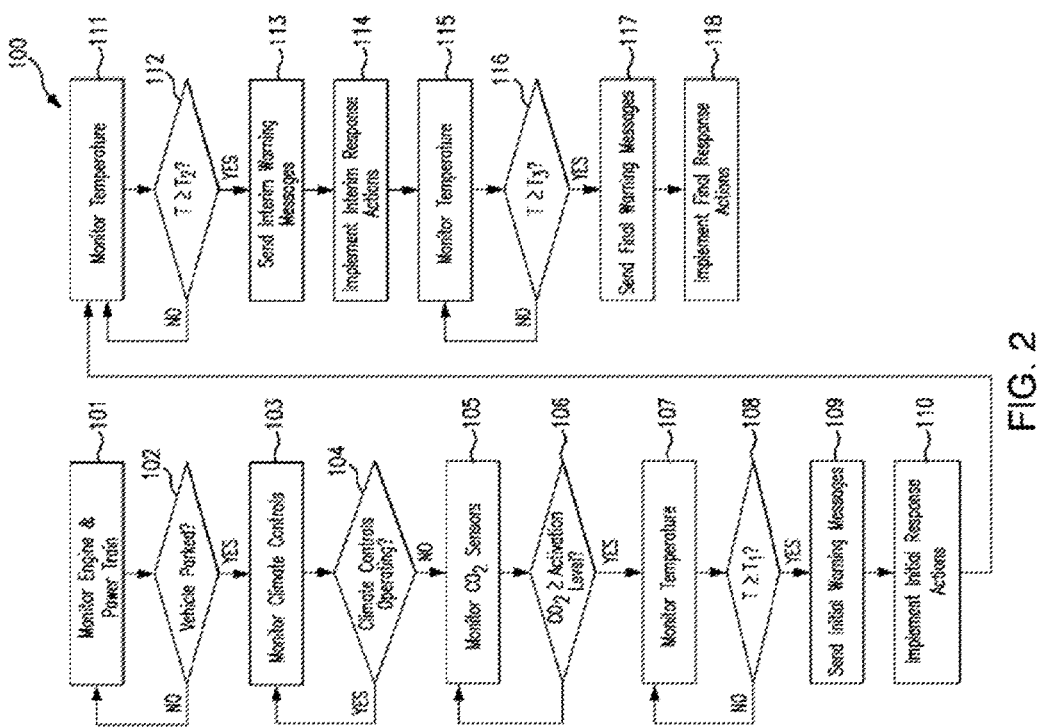
FIG. 2 is a flow chart depicting the method steps of one embodiment of the present invention.

FIG. 2 depicts the sequence of steps comprising an exemplary embodiment of the present invention 100. The central microprocessor 11 monitors the engine and power train 101 to determine if the vehicle is parked 102. If so, the central microprocessor 11 also monitors the climate controls 103 to determine if they are operating 104. If not, the central microprocessor 11 monitors the $CO_2$ sensors 104 and compares the $CO_2$ concentration readings for the passenger compartment with an activation level indicative of the presence of occupants 106. If occupancy is detected, the central microprocessor 11 monitors cabin temperature 107 and compares it with the lowest established emergency response temperature setpoint, designated in FIG. 2 as $T_1$ 108. If the first temperature setpoint is equaled or exceeded, initial warning messages are sent 109 and initial response actions are implemented 110.

The central microprocessor 11 then continues to monitor cabin temperatures 111, comparing it to the next lowest established emergency response temperature setpoint 112, designated as $T_2$ in FIG. 2. If the second temperature setpoint is equaled or exceeded, interim warning messages are sent 113 and interim response actions are implemented 114. The temperature monitoring continues 115, until the highest established emergency response temperature $T_3$ is equaled or exceeded 116, at which point the central microprocessor 11 sends the final warning messages 117 and implements the final response actions 118.

Figure 3:
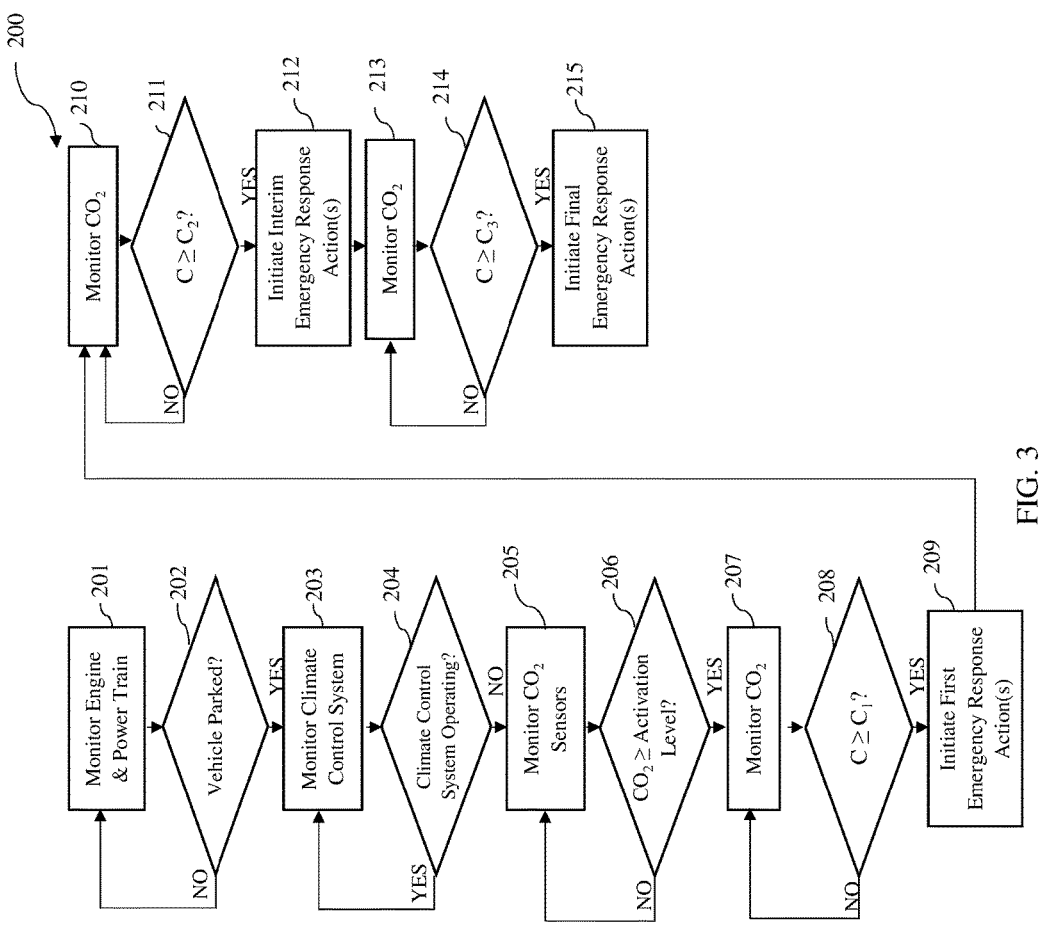
FIG. 3 is a flow chart depicting the method steps of another exemplary embodiment of the present invention.

FIG. 3 depicts the sequence of steps of another exemplary embodiment 200. The central microprocessor 11 monitors the engine and power train 201 to determine if the vehicle is parked 202. If so, the central microprocessor 11 also monitors the climate controls 203 to determine if they are operating 204. If not, the central microprocessor 11 monitors the $CO_2$ sensors 205 and compares the $CO_2$ concentration level of the passenger compartment with a $CO_2$ activation level indicative of the presence of occupants 206. For example, the central microprocessor may be programmed so that $CO_2$ concentration levels between 350-1000 parts per million (ppm) indicate an occupied cabin with adequate air exchange. If occupancy is detected, the central microprocessor 11 continues to evaluate the $CO_2$ concentration levels within the passenger compartment of the vehicle 207. If the $CO_2$ concentration levels equal or exceed a first $CO_2$ concentration setpoint 208, designated as $C_1$ in FIG. 3, the first emergency response action(s) may be implemented 209. For example, when the $CO_2$ sensors detect a $CO_2$ concentration level at or exceeding 2500 ppm, the central microprocessor may direct the climate control system to circulate fresh air from an outside source. The first emergency response action(s) may also include the transmission of a wireless message, such as a text or voice call, to a designated contact that alerts the designated contact of the status of the vehicle.

The central microprocessor 11 may then continue to monitor cabin $CO_2$ concentration levels 210, comparing the representative data generated by the $CO_2$ sensors to the next lowest established emergency response $CO_2$ concentration setpoint, $C_2$ as designated in FIG. 3 211. If the representative data on $CO_2$ concentration equals or exceeds $C_2$, interim response action(s) may be implemented 212. The $CO_2$ concentration level monitoring may continue 213 until the highest established emergency response $CO_2$ concentration setpoint, $C_3$, is equaled or exceeded 214. At that point, the central microprocessor may initiate the final emergency response action(s) 215.

The emergency response actions may be preprogrammed so that more aggressive actions will be taken at each increasing $CO_2$ concentration setpoint. For example, detection of $CO_2$ levels exceeding an emergency $CO_2$ concentration setpoint of 2500 ppm might trigger the transmission of a wireless message to the vehicle's owner, while detection exceeding an emergency setpoint of 50000 ppm may send a warning message and GPS coordinates to the local police.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method of protecting occupants in a passenger compartment of a vehicle, comprising:
    (a) equipping the vehicle with a central microprocessor which monitors the status of and controls the operations of multiple vehicle systems, including an engine, power train, one or more batteries, a climate control system, multiple windows, multiple doors, one or more sound-producing devices, and one or more emergency lights;
    (b) equipping the vehicle with one or more carbon dioxide (CO2) sensors distributed within the passenger compartment, which are controlled by the central microprocessor and which generate representative data on CO2 concentration within the passenger compartment;
    (c) equipping the vehicle with a wireless communication module, which is controlled by the central microprocessor and which sends and receives wireless messages;
    (d) providing one or more interfaces between the central microprocessor, the CO2 sensors and the wireless communication module, wherein the interfaces transmit the representative data on CO2 concentration to the central microprocessor and allow the central microprocessor to communicate with the wireless communication module;
    (e) determining and storing in the central microprocessor an activation CO2 concentration level, which is indicative of a presence of one or more occupants in the passenger compartment;
    (f) establishing and storing in the central microprocessor a progressive series of emergency response CO2 concentration setpoints, comprising a first CO2 concentration setpoint, a maximum CO2 setpoint and one or more intermediate CO2 concentration setpoints between the first CO2 concentration setpoint and the maximum CO2 concentration setpoint;
    (g) formulating and storing in the central microprocessor a progressive series of emergency response actions that correspond to each of the emergency response CO2 concentration setpoints, wherein one or more first emergency response actions correspond to the first CO2 concentration setpoint, one or more final emergency response actions correspond to the maximum CO2 concentration setpoint, and one or more interim emergency response actions correspond to each of the intermediate CO2 concentration setpoints;
    (h) activating the CO2 sensors, independent of temperature and other variables, once the central microprocessor determines, based on the status of the engine, the power train, and the climate control system, that the vehicle is parked and that the climate control system is not operating;
    (i) generating representative data on CO2 concentration levels and comparing the representative data with the activation CO2 concentration level stored in the central microprocessor to determine the presence of one or more occupants within the passenger compartment;

(j) when the representative data on CO2 concentration levels equals or exceeds the activation CO2 concentration level, determining at least one occupant is present in the passenger compartment and using the central microprocessor to compare CO2 concentration levels generated by the CO2 sensors with the emergency response CO2 concentration setpoints;

(k) initiating the first emergency response actions when the CO2 concentration levels equal or exceed the first CO2 concentration setpoint, independent of other variables;

(l) initiating the interim emergency response actions when the CO2 concentration levels equal or exceed one of the intermediate CO2 concentration setpoints, independent of other variables; and (m) initiating the final emergency response actions when the CO2 concentration levels equal or exceed the maximum CO2 concentration setpoint, independent of other variables.

2. The method of claim 1, wherein the progressive series of emergency response actions comprise transmitting a wireless message to one or more designated contacts via the wireless communication module.

3. The method of claim 2, wherein the progressive series of emergency response actions further comprise one or more safety precautions, including opening the multiple windows, unlocking the multiple doors, triggering the one or more sound-producing devices, and activating the one or more emergency lights.

4. The method of claim 1, wherein the climate control system includes one or more fans, which circulate ambient air through the passenger compartment and wherein one of the emergency response actions includes activation of one or more of the fans.

5. The method of claim 1, further comprising a GPS module, which receives satellite GPS coordinates of a location of the vehicle and a GPS interface, which interacts with the central microprocessor.

6. The method of claim 5, wherein the progressive series of emergency response actions include transmitting the GPS coordinates of the location of the vehicle through the wireless communication module to one or more designated contacts.

7. The method of claim 1, further comprising:

causing the central microprocessor to start the engine when the batteries are discharged below a designated level.

8. The method of claim 1, further comprising:

equipping the vehicle with one or more temperature sensors which are controlled by the central microprocessor and which monitor the temperature in the passenger compartment and generate temperature data; and establishing and storing in the central microprocessor a progressive series of emergency response temperature setpoints, comprising a first temperature setpoint, a maximum temperature setpoint, and one or more intermediate temperature setpoints between the first temperature setpoint and the maximum temperature set point.

9. The method of claim 8, wherein the central microprocessor activates the temperature sensors when the representative data on CO2 concentration levels equals or exceeds the activation CO2 concentration level.

10. The method of claim 9, further comprising:

using the central microprocessor to compare temperature data generated by the temperature sensors with the emergency response temperature setpoints;

when the central microprocessor determines that the temperature data equals or exceeds the first temperature setpoint, causing the central microprocessor to transmit, through the wireless communication module, the initial warning messages to one or more designated initial contacts, and causing the central microprocessor to implement the initial response actions;

when the central microprocessor determines that the temperature data equals or exceeds one of the intermediate temperature setpoints, causing the central microprocessor to transmit, through the wireless communication module, the corresponding interim warning messages to one or more designated interim contacts, and causing the central microprocessor to implement the corresponding interim response actions; and when the central microprocessor determines that the temperature data equals or exceeds the maximum temperature setpoint, causing the central microprocessor to transmit, through the wireless telecommunication module, the final warning messages to one or more designated final contacts, and causing the central microprocessor to implement the final response actions.

* * * * *